United States Patent
Keen

(10) Patent No.: US 11,679,211 B2
(45) Date of Patent: *Jun. 20, 2023

(54) METHOD FOR MEASURING A VAPOR PRECURSOR LEVEL IN A CARTOMIZER OF AN ELECTRONIC VAPING DEVICE AND/OR AN ELECTRONIC VAPING DEVICE CONFIGURED TO PERFORM THE METHOD

(71) Applicant: Altria Client Services LLC, Richmond, VA (US)

(72) Inventor: Jarrett Keen, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 626 days.

This patent is subject to a terminal disclaimer.

(21) Appl. No.: 16/732,694

(22) Filed: Jan. 2, 2020

(65) Prior Publication Data
US 2020/0128876 A1  Apr. 30, 2020

Related U.S. Application Data

(62) Division of application No. 14/819,946, filed on Aug. 6, 2015, now Pat. No. 10,524,505.

(51) Int. Cl.
*A61M 15/06* (2006.01)
*A61M 11/04* (2006.01)
(Continued)

(52) U.S. Cl.
CPC ............ *A61M 15/06* (2013.01); *A24F 40/44* (2020.01); *A24F 40/48* (2020.01); *A24F 40/50* (2020.01);
(Continued)

(58) Field of Classification Search
CPC ..... A61M 15/06; A61M 11/042; A24F 40/48; A24F 40/44; A24F 40/50
(Continued)

(56) References Cited

U.S. PATENT DOCUMENTS

| | | | | |
|---|---|---|---|---|
| 2 A | * | 7/1836 | Goulding | D01G 21/00 57/58.49 |
| 201 A | * | 5/1837 | Stanton | H04B 1/717 62/345 |

(Continued)

FOREIGN PATENT DOCUMENTS

| | | |
|---|---|---|
| CN | 1205849 A | 1/1999 |
| CN | 101969800 A | 2/2011 |

(Continued)

OTHER PUBLICATIONS

Notice of Allowance dated Jan. 8, 2021 issued in corresponding Chinese Patent Application No. 201680042456.1.

(Continued)

*Primary Examiner* — Alexander Gilman
(74) *Attorney, Agent, or Firm* — Harness, Dickey & Pierce, P.L.C.

(57) ABSTRACT

An electronic vaping device includes a cartomizer and a battery section. The cartomizer includes a housing, a liquid supply reservoir in the housing, a vaporizer connected to the liquid supply reservoir, a channel adjacent to the liquid supply reservoir. The liquid supply reservoir being is to store vapor precursor. The vaporizer includes a fluid-transport structure that is configured to transport the vapor precursor from the liquid supply reservoir to the channel. The battery section is configured to provide power to the vaporizer. The battery section includes a control circuit that is configured to determine a saturation level of the vapor precursor on the fluid-transport structure based on an electrical resistance of the fluid-transport structure.

17 Claims, 8 Drawing Sheets

(51) Int. Cl.
*A24F 40/48* (2020.01)
*A24F 40/44* (2020.01)
*A24F 40/50* (2020.01)
*A24F 40/60* (2020.01)
*F22B 1/28* (2006.01)
*H05B 1/02* (2006.01)
*H05B 3/06* (2006.01)
*A24F 40/10* (2020.01)

(52) U.S. Cl.
CPC ........... *A24F 40/60* (2020.01); *A61M 11/042* (2014.02); *F22B 1/28* (2013.01); *H05B 1/0297* (2013.01); *H05B 3/06* (2013.01); *A24F 40/10* (2020.01); *A61M 2205/18* (2013.01); *A61M 2205/3317* (2013.01); *A61M 2205/3386* (2013.01); *A61M 2205/3653* (2013.01); *A61M 2205/50* (2013.01); *A61M 2205/52* (2013.01); *A61M 2205/8206* (2013.01)

(58) Field of Classification Search
USPC .......................................................... 392/395
See application file for complete search history.

(56) References Cited

U.S. PATENT DOCUMENTS

| | | | | |
|---|---|---|---|---|
| 4,995,547 | A * | 2/1991 | Schubert | C04B 37/026 228/217 |
| 5,093,894 | A * | 3/1992 | Deevi | A24F 40/46 392/404 |
| 5,880,439 | A * | 3/1999 | Deevi | H01C 17/30 219/535 |
| 7,117,867 | B2 * | 10/2006 | Cox | A61M 11/042 128/200.14 |
| 8,205,622 | B2 * | 6/2012 | Pan | A24F 40/51 131/273 |
| 8,707,965 | B2 * | 4/2014 | Newton | A24F 40/485 131/194 |
| 10,111,281 | B2 * | 10/2018 | Qiu | A24F 40/60 |
| 10,524,505 | B2 * | 1/2020 | Keen | A24F 40/48 |
| 2004/0173228 | A1 * | 9/2004 | Coleman, III | A24B 15/22 131/347 |
| 2006/0011733 | A1 * | 1/2006 | Varanasi | A01M 1/205 239/4 |
| 2006/0196518 | A1 | 9/2006 | Hon | |
| 2006/0234232 | A1 * | 10/2006 | Narimatsu | C12N 9/1051 435/325 |
| 2009/0289197 | A1 * | 11/2009 | Slocum | H01J 37/08 250/424 |
| 2011/0265806 | A1 | 11/2011 | Alarcon et al. | |
| 2013/0087160 | A1 * | 4/2013 | Gherghe | A24F 40/90 131/329 |
| 2013/0192615 | A1 | 8/2013 | Tucker et al. | |
| 2013/0192616 | A1 | 8/2013 | Tucker et al. | |
| 2013/0192619 | A1 | 8/2013 | Tucker et al. | |
| 2013/0192620 | A1 | 8/2013 | Tucker et al. | |
| 2013/0192621 | A1 | 8/2013 | Li et al. | |
| 2013/0192622 | A1 | 8/2013 | Tucker et al. | |
| 2013/0192623 | A1 * | 8/2013 | Tucker | A24F 40/70 131/329 |
| 2014/0014126 | A1 * | 1/2014 | Peleg | A24F 40/57 374/54 |
| 2014/0020693 | A1 * | 1/2014 | Cochand | A24F 40/53 131/273 |
| 2014/0020963 | A1 * | 1/2014 | Smith | B62D 55/06 180/9.48 |
| 2014/0096782 | A1 * | 4/2014 | Ampolini | A24F 40/60 131/328 |
| 2014/0238424 | A1 | 8/2014 | Macko et al. | |
| 2014/0338685 | A1 * | 11/2014 | Amir | H05B 1/0244 131/329 |
| 2015/0027472 | A1 * | 1/2015 | Amir | H02J 7/00038 131/329 |
| 2016/0120229 | A1 | 5/2016 | Tucker et al. | |
| 2016/0157523 | A1 * | 6/2016 | Liu | A61M 15/001 392/395 |
| 2016/0165956 | A1 | 6/2016 | Tucker et al. | |
| 2016/0165957 | A1 | 6/2016 | Tucker et al. | |
| 2016/0183598 | A1 | 6/2016 | Tucker et al. | |
| 2016/0183599 | A1 | 6/2016 | Tucker et al. | |
| 2016/0374397 | A1 * | 12/2016 | Jordan | G01R 31/66 131/329 |
| 2017/0027234 | A1 * | 2/2017 | Farine | H05B 1/0244 |
| 2017/0035110 | A1 * | 2/2017 | Keen | A24F 40/48 |
| 2019/0104763 | A1 * | 4/2019 | Tucker | A24B 15/167 |
| 2021/0392954 | A1 * | 12/2021 | Blackmon | A24F 40/46 |

FOREIGN PATENT DOCUMENTS

| | | |
|---|---|---|
| CN | 103271446 A | 9/2013 |
| CN | 103338663 A | 10/2013 |
| CN | 103338665 A | 10/2013 |
| CN | 203618789 U | 6/2014 |
| CN | 204070530 U | 1/2015 |
| CN | 104812260 A | 7/2015 |
| CN | 105473011 A | 4/2016 |
| EP | 0970627 A1 | 1/2000 |
| EP | 2468117 A1 | 6/2012 |
| GR | 20120100199 A | 11/2013 |
| JP | 2000041654 A | 2/2000 |
| JP | 2014501105 A | 1/2014 |
| KR | 20120051570 A | 5/2012 |
| RU | 2389419 C2 | 5/2010 |
| WO | WO-2011/146174 A2 | 11/2011 |
| WO | WO-2012/085203 A1 | 6/2012 |
| WO | WO-2014-066730 A1 | 5/2014 |
| WO | WO-2015/015431 A1 | 2/2015 |

OTHER PUBLICATIONS

International Search Report dated Oct. 14, 2016 issued in corresponding International Application No. PCT/EP2016/068814.
Written Opinion dated Oct. 14, 2016 issued in corresponding International Application No. PCT/EP2016/068814.
Notice of Allowance and Search Report dated Sep. 26, 2019, issued in corresponding Russian Application No. 2018107723/12.
Office Action dated Apr. 28, 2020, issued in corresponding Chinese Patent Application No. 201680042456.1.
Notice of Allowance dated Jan. 4, 2021 issued in corresponding Japanese Patent Application No. 2018-505456.
Written Opinion dated Jun. 30, 2017 issued in corresponding International Application No. PCT/EP2016/068814.
Office Action dated Sep. 17, 2020, issued in corresponding Japan Patent Application No. 2018-505456.

* cited by examiner

METHOD FOR MEASURING A VAPOR PRECURSOR LEVEL IN A CARTOMIZER OF AN ELECTRONIC VAPING DEVICE AND/OR AN ELECTRONIC VAPING DEVICE CONFIGURED TO PERFORM THE METHOD

CROSS-REFERENCE TO RELATED APPLICATION

This application is a divisional of U.S. application Ser. No. 14/819,946, filed Aug. 6, 2015, the entire contents of which are hereby incorporated by reference.

BACKGROUND

Field

The present disclosure relates to an electronic vaping device and/or more particularly to an electronic vaping device configured to measure a vapor precursor level in a cartomizer.

Related Art

Electronic vaping devices (also referred to as e-vaping devices) may be used to vaporize a liquid material into a "vapor" in order to permit vaping by an adult vaper. The liquid material may be referred to as a vapor precursor. An electronic vaping device may include several elements, such as a power source and a cartomizer (also referred to as a cartridge). The power source may be a battery section. The cartomizer may include a reservoir for holding the vapor precursor and a heater for vaporizing the vapor precursor to produce a vapor. The vapor precursor in the cartomizer may be consumed when the electronic vaping device generates a vapor in response to an adult vaper applying negative pressure to a mouthpiece of the electronic vaping device (e.g., a puff).

As the vapor precursor is consumed, the level of the vapor precursor in the cartomizer decreases. When the vapor precursor in the cartomizer is consumed below a threshold level, the cartomizer may be replaced with a new cartomizer that contains a reservoir holding vapor precursor.

SUMMARY

The present disclosure relates to an electronic vaping device and/or more particularly an electronic vaping device configured to measure a vapor precursor level in a cartomizer.

According to example embodiments, an electronic vaping device includes a cartomizer and a battery section. The cartomizer includes a housing, a liquid supply reservoir in the housing, a vaporizer connected to the liquid supply reservoir, a channel adjacent to the liquid supply reservoir. The liquid supply reservoir is configured to store vapor precursor. The vaporizer includes a fluid-transport structure that is configured to transport the vapor precursor from the liquid supply reservoir to the channel. The battery section is configured to provide power to the vaporizer. The battery section includes a control circuit that is configured to determine a saturation level of the vapor precursor on the fluid-transport structure based on an electrical resistance of the fluid-transport structure.

In example embodiments, the cartomizer and the battery section may be configured to be removably coupled to each other. The vaporizer may include a heating element that is configured to generate a vapor from the vapor precursor transported to the channel.

In example embodiments, the battery section may include a battery. The fluid-transport structure may include a wick that extends from the channel into the liquid supply reservoir. The heating element may include a heating coil that is wrapped around a part of the wick. The heating coil may be configured to receive power from the battery and heat the wick.

In example embodiments, the cartomizer may include a first electrical lead and a second electrical lead that are connected to respective ends of the heating coil. The cartomizer may include a first probe connected to a first end of the wick. The first probe and the first electrical lead may be separated from each other. The control circuit may be configured to measure the electrical resistance across a portion of the wick using the first probe and one of the first and second electrical leads. The control circuit may be configured to determine the saturation level of the vapor precursor on the fluid-transport structure based on the measured electrical resistance of the portion of the wick.

In example embodiments, the cartomizer may include a first probe and a second probe that are electrically connected to a first end and a second end of the wick, respectively. The battery section may be configured to connect the first and second probes to the control circuit. The control circuit may be configured to measure the electrical resistance across the wick using the first probe and the second probe.

In example embodiments, the cartomizer may include a first probe and a second probe that are electrically connected to a first end and a second end of the wick, respectively. The cartomizer may include a first electrical lead and a second electrical lead that are connected to respective ends of the heating coil. The first probe and the first electrical lead may be separated from each other. The second probe and the second electrical lead may be separated from each other. The control circuit may be configured to measure the electrical resistance across the first portion of the wick using the first probe and at least one of the first and second electrical leads. The control circuit may be configured to measure the electrical resistance across the second portion of the wick using the first probe and the second probe. The control circuit may be configured to determine the saturation level of the vapor precursor on the fluid-transport structure based on at least one of the measured electrical resistance across the first portion of the wick and the measured electrical resistance across the second portion of the wick. The first portion of the wick and the second portion of the wick may be different sizes.

In example embodiments, the control circuit may be configured to measure the electrical resistance across a third portion of the wick using the second probe and at least one of the first and second electrical leads. The second portion and the third portion of the wick may be different sizes.

In example embodiments, the electronic vaping device may further include a LED. The control circuit may be connected to the LED. The control circuit may be configured to control the LED to display a first color if the electrical resistance of the fluid-transport structure is between a first threshold value and a second threshold value. The control circuit may be configured to control the LED to display a second color if the electrical resistance of the fluid-transport structure is greater than the first threshold value. The first threshold value may be greater than the second threshold value. The first color may be different than the second color.

In example embodiments, the control circuit may be configured to limit the supply of power to the vaporizer if the electrical resistance of the fluid-transport structure is greater than the first threshold value.

In example embodiments, the control circuit may include a resistive sensing unit and a vaporizer driver.

In example embodiments, the control circuit may include a memory unit. The memory unit may be configured to store a plurality of electrical resistance values that correspond to the electrical resistance the fluid-transport structure measured at different times. The control circuit may be configured to issue an alert based on a comparison result of at least two of the electrical resistance values measured from the fluid-transport structure of the same cartomizer.

In example embodiments, the at least two of the electrical resistance values may include a first value and a second value. The control circuit may be configured to issue the alert if a ratio based on the first value and the second value is greater than a threshold ratio, and/or a difference based on the first value and the second value is greater than a threshold difference.

According to example embodiments, a battery section of an electronic vaping device may include a battery and a control circuit connected to the battery. The control circuit may be configured to determine a saturation level of the vapor precursor on a fluid-transport structure based on the electrical resistance of at least a portion of the fluid-transport structure.

In example embodiments, the battery section may be configured to be removably coupled to a cartomizer of the electronic vaping device.

In example embodiments, the control circuit may be configured to limit the supply of power that the battery supplies to an external device if the control circuit determines the electrical resistance is greater than a threshold value.

In example embodiments, the battery section may further include a LED connected to the battery. The control circuit may be configured to control the LED to display a first color if the electrical resistance is between a first threshold value and the second threshold value. The control circuit may be configured to control the LED to display a second color if the electrical resistance of the fluid-transport structure is greater than the first threshold value. The first threshold value may be greater than the second threshold value. The first color may be different than the second color.

In example embodiments, the control circuit may include a resistive sensing controller and a vaporizer driver. The vaporizer driver may be configured to control supply and power to a vaporizer if the vaporizer driver is electrically connected to the vaporizer. The resistive sensing controller may be configured to determine the electrical resistance based on sensing resistance values measured at different positions of the fluid-transport structure.

According to example embodiments, a cartomizer includes a housing, a liquid supply reservoir in the housing, a vaporizer connected to the liquid supply reservoir, a channel adjacent to the liquid supply reservoir, a first electrical lead and a second electrical lead connected to a first position and a second position of the vaporizer, and a probe connected to a third position of the vaporizer. The liquid supply reservoir is configured to store the vapor precursor. The vaporizer includes a fluid-transport structure that extends from the liquid supply reservoir into the channel and is configured to transport the vapor precursor from the liquid supply reservoir to the channel. The first, second, and third positions of the vaporizer are spaced apart from each other. The first electrical lead, second electrical lead, and the probe are spaced apart from each other.

In example embodiments, the vaporizer may include a heating element that is configured to generate a vapor from the vapor precursor transported to the channel. The first position and the second position of the vaporizer may be different ends of the heating element.

In example embodiments, the fluid-transport structure may include a wick that extends from the channel into the liquid supply reservoir. The heating element may surround a portion of the wick in the channel. The third position of the vaporizer may correspond to one end of the wick.

In example embodiments, the cartomizer may include a mouth-end insert and a seal in the housing at opposite ends of the housing. The first electrical lead and second electrical lead may extend from the first and second positions through the seal to one end of the housing.

In example embodiments, the probe may extend from the third position of the vaporizer to one end of the housing.

According to example embodiments, a method of operating an electronic device includes measuring an electrical resistance of a fluid-transport structure in a cartomizer of the electronic vaping device using a control circuit in a battery section of the electronic vaping device and determining a saturation level of the vapor precursor on the fluid-transport structure based on the electrical resistance measurement of the fluid-transport structure. The cartomizer includes a housing, a liquid supply reservoir in the housing, a vaporizer connected to the liquid supply reservoir, and a channel adjacent to the liquid supply reservoir. The vaporizer includes the fluid-transport structure. The fluid-transport structure is configured to transport vapor precursor from the liquid supply reservoir to the channel.

In example embodiments, the method may further include issuing an alarm or re-measuring the electrical resistance after an adult vapor vaper applies negative pressure to the electronic vaping device at least one time, based on the electrical resistance measurement.

In example embodiments, the determining the saturation level may include determining if the electrical resistance measurement is less than a threshold value. The issuing the alarm may be performed if the electrical resistance measurement is greater than the threshold value. The re-measuring the electrical resistance after the adult vaper applies negative pressure to the electronic vaping device at least one time may be performed if the electrical resistance measurement is less than or equal to the threshold value.

In example embodiments, the determining the saturation level may include determining if the electrical resistance measurement is between a first threshold value and a second threshold value. The first threshold value may be greater than the second threshold value. The re-measuring the electrical resistance after the adult vaper applies negative pressure to electronic vaping device at least one time may be performed if the electrical resistance measurement is between the first and second threshold values.

In example embodiments, the cartomizer and the battery section may be configured to be removably coupled to each other. The vaporizer may include a heating element that is configured to generate a vapor from the vapor precursor transported to the channel.

According to example embodiments, a method of making an electronic vaping device includes connecting a cartomizer to a battery section. The cartomizer includes a housing, a liquid supply reservoir in the housing, a vaporizer connected to the liquid supply reservoir, and a channel adjacent to the liquid supply reservoir. The liquid supply reservoir is configured to store the vapor precursor. The vaporizer includes a fluid-transport structure that is configured to transport the vapor precursor from the liquid supply reservoir to the channel. The battery section is configured to provide power to the vaporizer. The battery section includes a control circuit that is configured to determine a saturation level of the vapor precursor on the fluid-transport structure based on an electrical resistance of the fluid-transport structure.

In example embodiments, the cartomizer and the battery section may be configured to be removably coupled to each other, and the vaporizer may include a heating element that is configured to generate a vapor from the vapor precursor transported to the channel.

In example embodiments, the battery section may include a battery, the fluid-transport structure may include a wick that extends from the channel into the liquid supply reservoir, the heating element may include a heating coil that is wrapped around a part of the wick, and a heating coil may be configured to receive power from the battery and heat the wick.

In example embodiments, the cartomizer may include a first electrical lead and a second electrical lead that are connected to respective ends of the heating coil. The cartomizer may include a first probe connected to a first end of the wick. The first probe and the first electrical lead may be separated from each other. The control circuit may be configured to measure the electrical resistance across a portion of the wick using the first probe and one of the first and second electrical leads. The control circuit may be configured to determine the saturation level of the vapor precursor on the fluid-transport structure based on the measured electrical resistance of the portion of the wick.

In example embodiments, the cartomizer may include a first probe and the second probe that are electrically connected to a first end and a second end of the wick, respectively. The battery section may be configured to connect the first and second probes to the control circuit. The control circuit may be configured to measure the electrical resistance across the wick using the first probe and the second probe.

In example embodiments the cartomizer may include a first probe and a second probe that are electrically connected to a first end and a second end of the wick, respectively. The cartomizer may include a first electrical lead and the second electrical lead that are connected to respective ends of the heating coil. The first probe and the first electrical lead may be separated from each other. The second probe and the second electrical lead may be separated from each other. The control circuit may be configured to measure the electrical resistance across the first portion of the wick using the first probe and one of the first and second electrical leads. The control circuit may be configured to measure the electrical resistance across the second portion of the wick using the first probe and the second probe. The control circuit may be configured to determine the saturation level of the vapor precursor on the fluid-transport structure based on at least one of the measured electrical resistance across the first portion of the wick and the measured electrical resistance across the second portion of the wick. The first portion of the wick and the second portion of the wick may be different sizes.

In example embodiments, the control circuit may be configured to measure the electrical resistance across the third portion of the wick using the second probe and at least one of the first and second electrical leads. The second portion and the third portion of the wick may be different sizes.

BRIEF DESCRIPTION OF THE DRAWINGS

The above and other features and advantages of example embodiments will become more apparent by describing in detail, example embodiments with reference to the attached drawings. The accompanying drawings are intended to depict example embodiments and should not be interpreted to limit the intended scope of the claims. The accompanying drawings are not to be considered as drawn to scale unless explicitly noted.

DETAILED DESCRIPTION

Figure 1A:
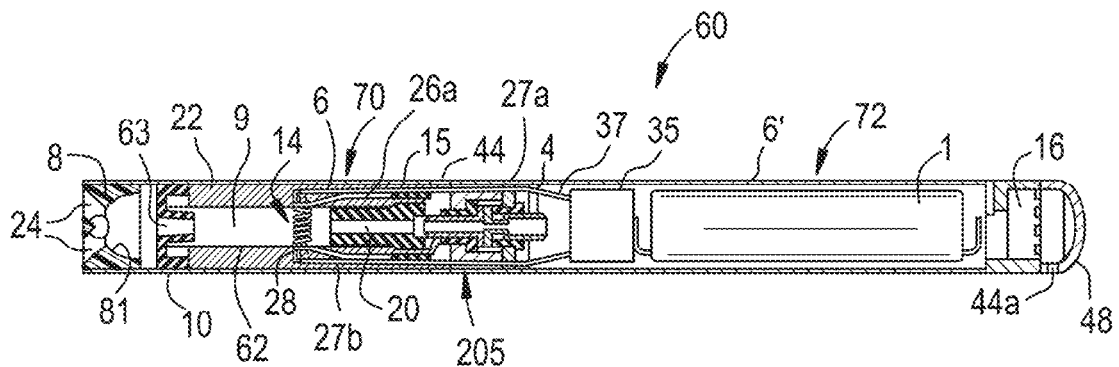
FIGS. 1A and 1B are cross-sectional views of an electronic vaping device according to example embodiments.

Some detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Throughout the illustrative description, the examples, and the appended claims, a numerical value of a parameter, feature, object, or dimension, may be stated or described in terms of a numerical range format. It is to be fully understood that the stated numerical range format is provided for illustrating implementation of the forms disclosed herein, and is not to be understood or construed as inflexibly limiting the scope of the forms disclosed herein.

Moreover, for stating or describing a numerical range, the phrase "in a range of between about a first numerical value and about a second numerical value," is considered equivalent to, and means the same as, the phrase "in a range of from about a first numerical value to about a second numerical value," and, thus, the two equivalently meaning phrases may be used interchangeably.

A vapor precursor is a material or combination of materials that may be transformed into a vapor. For example, the vapor precursor may be a liquid, solid and/or gel formulation including, but not limited to, water, beads, solvents, active ingredients, ethanol, plant extracts, natural or artificial flavors, and/or vapor formers such as glycerin and propylene glycol. For example, the vapor precursor may be a pre-vaporization formulation, where a vapor may be generated from the pre-vaporization formulation by heating the vaporization formulation above a threshold temperature (e.g., a boiling point of the pre-vaporization formulation).

When the terms "about" or "substantially" are used in this specification in connection with a numerical value, it is intended that the associated numerical value include a tolerance of ±10% around the stated numerical value unless the context indicates otherwise. Moreover, unless the context indicates otherwise, when reference is made to percentages in this specification, it is intended that those percentages are based on weight, i.e., weight percentages. The expression "up to" includes amounts of zero to the expressed upper limit and all values therebetween. When ranges are specified, the range includes all values therebetween such as increments of 0.1%.

Examples of electronic vaping devices are described in US Patent Publication Nos. 2013/0192623 and US 2014/0238424, the entire contents of each of which are incorporated herein by reference.

Figure 1B:
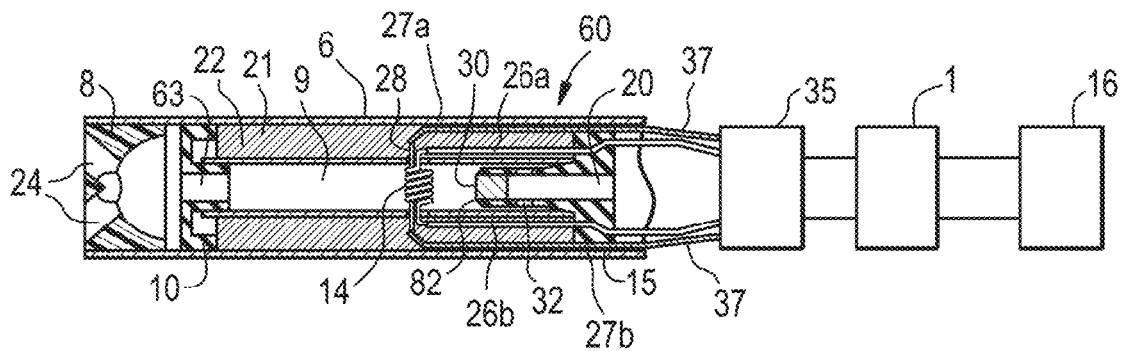
Figure 1C:
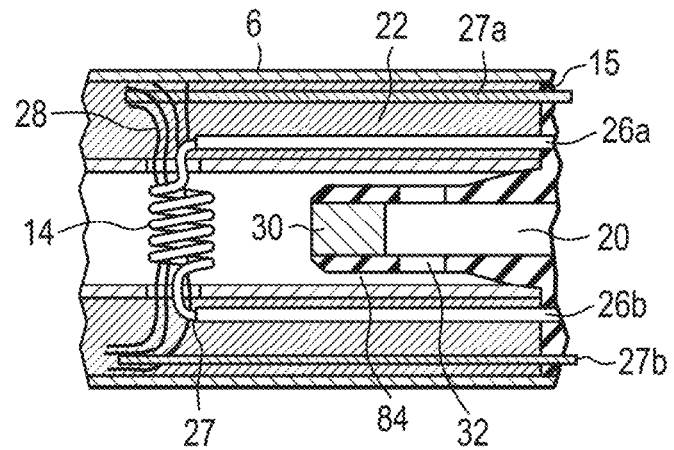
FIG. 1C is an enlarged view of a portion of the cartomizer of the electronic vaping device of FIGS. 1A and 1B.

FIGS. 1A and 1B are cross-sectional views of an electronic vaping device according to example embodiments. FIG. 1C is an enlarged view of a portion of the cartomizer of the electronic vaping device of FIGS. 1A and 1B.

According to example embodiments, an electronic vaping device 60 may include a cartomizer 70 (also referred to as a tank or cartridge) and a battery section 72. The cartomizer 70 may include an outer housing 6. The battery section 72 may include an outer casing 6'. The housing 6 and/or outer casing 6' may be tubular in shape, but are not limited thereto and may be other shapes. The cartomizer 70 and the battery section 72 may be removably coupled together using a threaded connection 205 or removably coupled together using another arrangement such as a snug-fit, detent, clamps and/or clasps. The cartomizer 70 may be replaceable. The battery section 72 may be reusable. Alternatively, instead of a separate housing 6 and casing 6' for the cartomizer 70 and the battery section 72, respectively, a single casing may enclose both the cartomizer 70 and the battery section 72. In which case, the entire electronic vaping device 60 may be disposable.

Because the cartomizer 70 and the battery section 72 may be removably coupled to each other, a method of making an electronic vapor device according to example embodiments may include connecting the cartomizer 70 and battery section 72 to each other.

One end of the cartomizer 70 may include a power supply connector 4. The power supply connector 4 may be a battery connector. The other end of the cartomizer 70 may include a mouth-end insert 8. The mouth-end of the electronic vaping device 60 may be considered the end of the electronic vaping device 60 where the mouth-end insert 8 is disposed. The mouth-end insert 8 may include at least two diverging outlets 24 (e.g., 2 to 10 outlets 24 or more). An interior surface 81 of the mouth-end insert 8 may be curved, but is not limited thereto. The diverging outlets 24 of the mouth-end insert 8 may be in fluid communication with a central passage 63. The central passage 63 may be defined by an inner surface of a stopper 10 inside the housing 6.

The cartomizer may include a liquid supply reservoir 22 in the housing, a vaporizer connected to the liquid supply reservoir 22, and a channel 9 adjacent to the liquid supply reservoir 22. The liquid supply reservoir 22 may be contained in a region between the housing 6 and an inner casing 62 inside the housing 6. The liquid supply reservoir 22 may be configured to store vapor precursor 21.

For example, the liquid supply reservoir 22 may include a liquid storage material for storing the vapor precursor 21. The liquid storage material may be a fibrous material such as cotton, but example embodiments are not limited thereto. Optionally, the liquid storage material may be omitted from the liquid supply reservoir 22. The liquid supply reservoir 22 may be sealed at opposite ends by a stopper 10 and a seal 15 so as to limit and/or prevent leakage of the vapor precursor from the liquid supply reservoir 22. The channel 9 may be defined by an inner surface of the inner casing 62. Opposite ends of the channel 9 may be in fluid communication with the central passage 63 and a central air passage 20. Also, as shown in FIG. 1C, the cartomizer 70 may further include an air flow diverter such as an impervious plug 30 at a downstream end 82 of the central air passage 20. The air flow diverter 30 may include at least one radial air channel 32 directing air from the central passage 20 outward toward the inner casing 62 and into an outer air passage 84 defined between an outer periphery of a downstream end portion of the seal 15 and the inner wall of inner casing 62.

The vaporizer may include a fluid-transport structure that is configured to transport the vapor precursor 21 from the liquid supply reservoir 22 to the channel 9. The vaporizer may also be configured to generate a vapor from heating the vapor precursor 21 in the liquid supply reservoir 22. For example, the vaporizer may include a heating element 14 and at least one wick 28. The wick 28 may extend from one portion of the liquid supply reservoir 22 through the channel 9 into another portion of the liquid supply reservoir 22. The heating element 14 may be in the form of a wire coil, a planar body, a ceramic body, a single wire, a cage of resistive wire or any other suitable form. The heating element 14 may be wrapped around a part of the wick 28 such as a part of the wick 28 in the channel 9. The wick 28 (or a plurality of wicks 28) may be in communication with the vapor precursor 21 in the liquid supply reservoir 22 and in communication with the heating element 14 such that the wick 28 may dispose vapor precursor in proximate relation to the heating element 14.

The wick 28 may be constructed of a fibrous and flexible material. The wick 28 may include at least one filament that is configured to transport vapor precursor from the liquid supply reservoir 22 to the heating element 14 when an adult vaper applies negative pressure to the mouth end of the electronic vaping device 60. The wick 28 may be a bundle of filaments, such as a bundle of glass (or ceramic) filaments. The wick 28 may include a group of windings of glass filaments (e.g., three windings), all which arrangements are capable of drawing vapor precursor via capillary action via interstitial spacing between the filaments.

When an adult vaper applies negative pressure to the electronic vaping device 60, the wick 28 may transport vapor precursor 21 to the channel 9 and onto the heating element 14. The heating element 14 may be configured to generate a vapor from the vapor precursor 21 transported to the channel 9 based on heating the vapor precursor 21. For example, the heating element 14 may receive electrical power from a power supply 1 in the battery section 72 and heat vapor precursor 21 in proximate relation to the heating element 14 and/or on the heating element 14 through resistive heating. Also, the heating element 14 (e.g., a heating coil) may be configured to receive power from the power supply 1 and heat the wick 28.

The battery section 72 may be configured to provide power to the vaporizer. For example, the battery section 72 may include the power supply 1, a control circuit 35, and a puff sensor 16. The power supply connector 4 of the cartomizer 72 may connect to the power supply 1 directly (and/or indirectly through the control circuit 35 and/or lead wires). The power supply 1 may be a Lithium-ion battery or one of its variants, for example a Lithium-ion polymer battery. Alternatively, the battery may be a Nickel-metal hydride battery, a Nickel cadmium battery, a Lithium-manganese battery, a Lithium-cobalt battery or a fuel cell. The power supply 1 may be rechargeable and include circuitry allowing the battery to be chargeable by an external charging device.

Inside the housing 6 of the cartomizer 70, first and second leads 26a and 26b (e.g., wires) may electrically connect the power supply connector 4 to the heating element 14. The first and second leads 26a and 26b may extend in the liquid supply reservoir 22 from the power supply connector 4 through the seal 15 to respective ends of the heating element 14. The first and second leads 26a and 26b may connect to respective ends of the heating element 14.

The casing 6' may define at least one air inlet 44a positioned at the upstream end of the battery section 72 adjacent to the puff sensor 16. The puff sensor 16 may sense when an adult vaper applies negative pressure to the electronic vaping device 60. When an adult vaper applies negative pressure to the mouth end of the electronic vaping device 60, such action may draw air into the electronic vaping device 60 through the air inlet 44a to initiate the puff sensor 16 and may also draw air into the electronic vaping device 60 from air inlets 44 defined by the housing 6 of the cartomizer 60. The air inlet 44a may communicate with the mouth-end insert 8 so that a draw upon the mouth-end insert activates the puff sensor 16. The air from the air inlet 44a can then flow along the power supply 1 and to the central air passage 20 in the seal 15 and/or to other portions of the inner casing 62 and/or housing 6.

The control circuit 35 in the battery section 72 may direct the power supply 1 to supply power to heating element 14 if the puff sensor 16 senses a puff by an adult vaper. The control circuit 35 may also be connected to an activation light 48. The control circuit 35 may direct the activation light 48 to glow (e.g., turn on) when the heating element 14 receives power from the power supply 1. The activation light 48 may include a light-emitting device (LED) such as a diode, and may be at an upstream end of the electronic vaping device 60. The activation light 48 may provide the appearance of a burning coal when an adult vaper applies negative pressure to the mouth-end insert of the electronic vaping device 60. Moreover, the activation light 48 can be arranged to be visible to the adult vaper. In addition, the activation light 48 can be utilized for system diagnostics. The light 48 can also be configured such that the adult vaper can activate and/or deactivate the light 48 for privacy, such that the light 48 would not activate during vaping if desired.

The control circuit 35 may also be configured to determine a saturation level of the vapor precursor 21 on the wick 28 based on an electrical resistance of the wick 28. The vapor precursor 21 may be more electrically conductive than a material of the wick 28. As a result, when the wick 28 is saturated with vapor precursor 21, the electrical resistance measured across one or more portions (e.g., segments) of the wick 28 may be less than a state where the wick 28 is not saturated with vapor precursor 21. As the vapor precursor 21 is consumed, the wick 28 may become less saturated with vapor precursor 21. By measuring the electrical resistance across one or more portions of the wick 28, it is possible to determine when the level of vapor precursor 21 in the cartomizer 70 is low or empty and/or when the cartomizer 70 should be replaced with a new cartomizer 70 full of vapor precursor 21.

The control circuit 35 may be programmable and/or may include an application specific integrated circuit (ASIC). In other example embodiments, the control circuitry may include a microprocessor programmed to carry out functions of the control circuit 35.

As shown in FIGS. 1A to 1C, the cartomizer 70 may include a first probe 27a connected to a first end of the wick 28 and a second probe 27b connected to a second end of the wick 28, and the channel 9 may be in between the first and second ends of the wick 28. The first probe 27a and second probe 27b may be formed of electrically conductive materials (e.g., a metal) and may be surrounded by an insulating material. The first probe 27a and the first electrical lead 26a may be separated from each other. The second probe 27b and the second electrical lead 26b may be separated from each other.

The battery section 72 may be configured to connect the first and second probes 27a and 27b to the control circuit 35. For example, when the cartomizer 70 and battery section 72 are connected to each other, the electrical connector 37 may connect the first and second probes 27a and 27b to the control circuit 35.

Figure 2A:
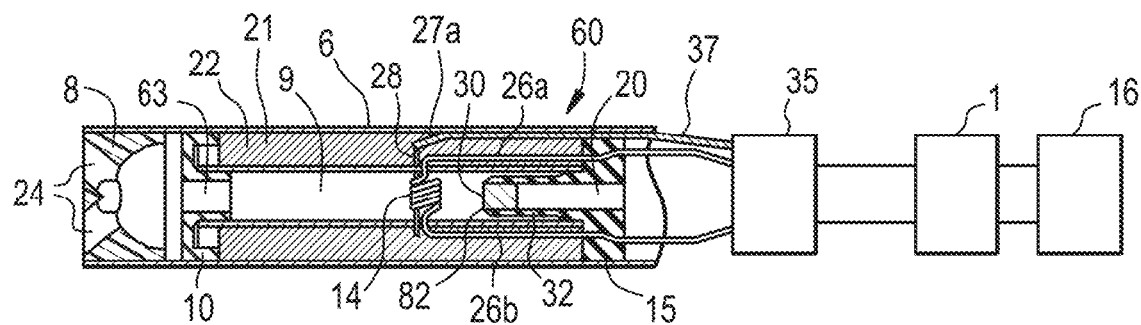
FIG. 2A is a cross-sectional view of an electronic vaping device according to example embodiments.
Figure 2B:
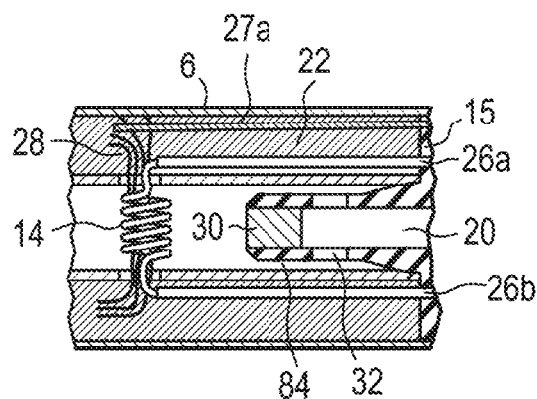
FIG. 2B is an enlarged view of a portion of the cartomizer in FIG. 2A.

FIG. 2A is a cross-sectional view of an electronic vaping device according to example embodiments. FIG. 2B is an enlarged view of a portion of the cartomizer in FIG. 2A.

Referring to FIGS. 2A and 2B, according to example embodiments, an electronic vaping device may be the same as the electronic vaping device described previously with reference to FIGS. 1A to 1C, except for the number of probes 27a and 27b connected to the wick 28 in the cartomizer 70.

As shown in FIGS. 2A and 2B, the cartomizer 70 may include the first probe 27a connected to the end of the wick that is adjacent to the first lead 26a. However, unlike the cartomizer 70 described in FIGS. 1A to 1C, the cartomizer 70 in FIGS. 2A and 2B may be constructed without the second probe 27b connected to the end of the wick that is adjacent to the second lead 26b.

Figure 2C:
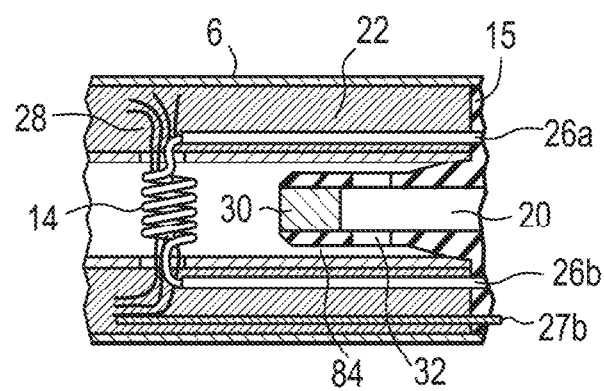
FIG. 2C is an enlarged view of a portion of a modification of the cartomizer in FIGS. 1A to 1C and 2A.

FIG. 2C is an enlarged view of a portion of a modification of the cartomizer in FIGS. 1A to 1C and 2A.

As shown in FIG. 2C, the cartomizer 70 may include the second probe 27b connected to the end of the wick that is adjacent to the second lead 26b. However, unlike the cartomizer 70 described in FIGS. 1A to 1C, the cartomizer 70 in FIGS. 2A and 2B may be constructed without the first probe 27a connected to the end of the wick that is adjacent to the first lead 26a.

Although FIGS. 1A to 1C, 2B, and 2C illustrate non-limiting examples where the first probe 27a and/or second probe 27b are connected to respective ends of the wick 28, one of ordinary skill in the art would appreciate that additional probes may be connected to other portions of the wick 28.

Figure 3A:
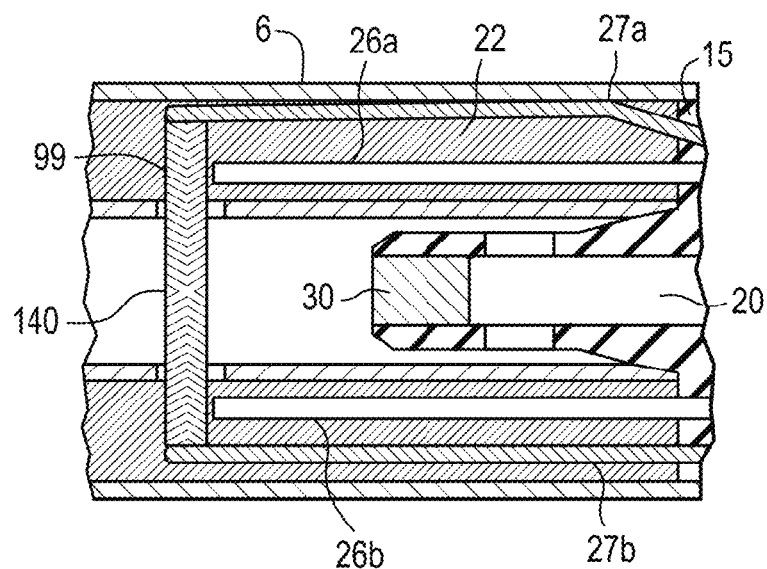
FIG. 3A is an enlarged view of a portion of a modified cartomizer of an electronic vaping device according to example embodiments.

FIG. 3A is an enlarged view of a portion of a modified cartomizer of an electronic vaping device according to example embodiments.

Referring to FIG. 3A, according to example embodiments, an electronic vaping device may be the same as the electronic vaping device described previously with reference to FIGS. 1A to 1C, except for the structure of the vaporizer in the cartomizer 70. As shown in FIG. 3A, the vaporizer may be a heater-wick structure 140 instead of the heating element 14 and wick 28 in the cartomizer 70 shown in FIG. 1A. The heater-wick structure 140 may be a plurality of small metal beads or particles that have been fused together, but is not limited thereto an may be formed of other materials. Opposite ends of the heater-wick structure 140 may extend into the liquid supply reservoir. A middle portion of the heater-wick structure 140 may be disposed in the channel 9.

As shown in FIG. 3A, the first probe 27a and the second probe 27b may be connected to the respective ends of the heater-wick structure 140 inside the liquid supply reservoir 22. The first lead 26a and the second lead 26b may be connected the heater-wick structure 140 at areas adjacent to where the first probe 27a and second probe 27b are connected to the heater-wick structure 140. Connection structures 99 (e.g., metal ring) may be used to secure the first and second leads 26a and 26b to the heater-wick structure 140. For example, the connection structure 99 may provide brazed connections between the heater-wick structure 140 and the first and second leads 26a and 26b. Although not shown in FIG. 3A, connection structures that are the same as or similar to the connection structures 99 may similarly be used to connect the first probe 27a and the second probe 27b to the heater-wick structure 140.

The first lead 26a and the first probe 27a may be spaced apart from each other in the liquid supply reservoir 22. The second lead 26b and the second probe 27b may be spaced apart from each other in the liquid supply reservoir 22. The location where the first lead 26a is connected to the heater-wick structure 140 may be spaced apart from the location where the first probe 27a is connected to the heater-wick structure 140. The location where the second lead 26b is connected to the heater-wick structure 140 may be spaced apart from the location where the second probe 27b is connected to the heater-wick structure 140.

Figure 3B:
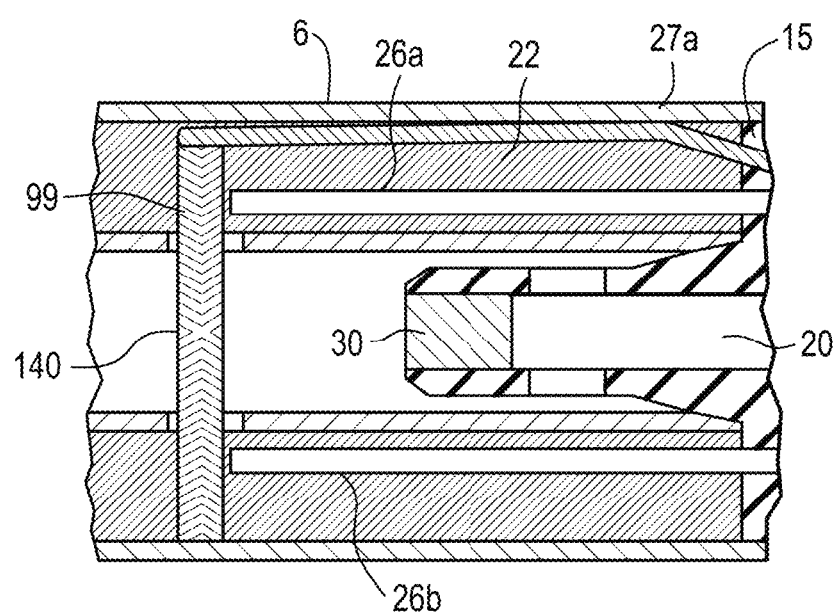
FIG. 3B is an enlarged view of a portion of a modified cartomizer of an electronic vaping device according to example embodiments.

FIG. 3B is an enlarged view of a portion of a modified cartomizer of an electronic vaping device according to example embodiments.

Referring to FIG. 3B, the cartomizer 70 may include the first probe 27a connected to the end of the heater-wick structure 140 that is adjacent to the first lead 26*a*. However, unlike the cartomizer 70 described in FIGS. 3A, the cartomizer 70 in FIG. 3B may be constructed without the second probe 27*b* connected to the end of the heater-wick structure 140 that is adjacent to the second lead 26*b*. Alternatively, the cartomizer 70 may be constructed with the second probe 27*b* connected to the end of heater-wick structure 140 that is adjacent to the second lead 26*b*, but without the first probe 27*a* connected to the heater-wick structure 140.

Although FIGS. 3A and 3B illustrate non-limiting examples where the first probe 27*a* and/or second probe 27*b* are connected to respective ends of the heater-wick structure 140, one of ordinary skill in the art would appreciate that additional probes may be connected to other locations of the heater-wick structure 140 and/or the locations where the leads 26*a* and 26*b* and probes 27*a* and 27*b* are connected to the heater-wick structure 140 may be variously modified.

Figure 4A:
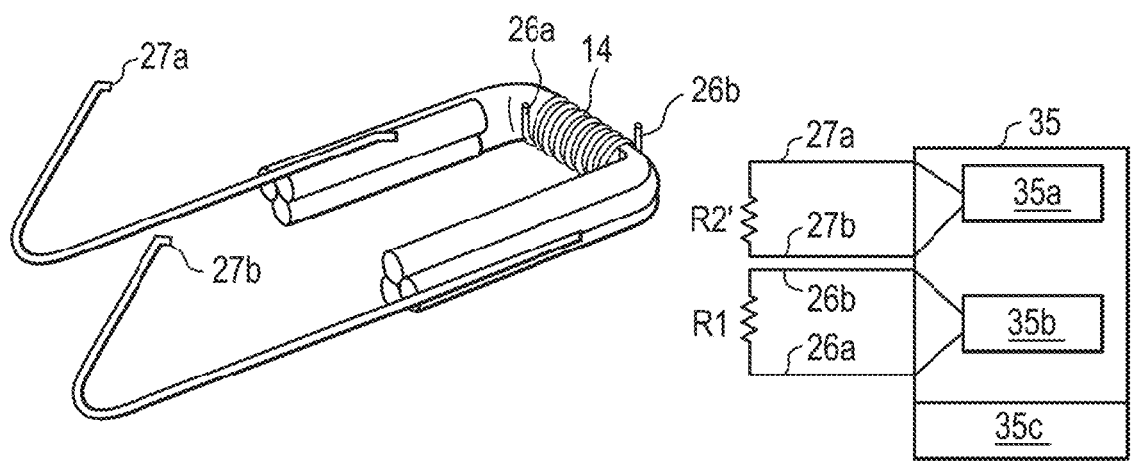
FIG. 4A is a diagram illustrating an electrical connection between a control circuit and a wick in an electronic vaping device according to example embodiments.

FIG. 4A is a diagram illustrating an electrical connection between a control circuit and a wick in an electronic vaping device according to example embodiments.

Referring to FIG. 4A, the wick 28 may include first and second probes 27*a* and 27*b* connected to respective ends of the wick 28, a heating-element (e.g., coil) 14 wrapped around a central portion of the wick 28, and first and second leads 26*a* and 26*b* connected to respective ends of the heating element 14. The first and second leads 26*a* may contact or be adjacent to parts of the wick 28 between the locations where the probes 27*a* and 27*b* are connected to the wick 28.

The probes 27*a* and 27*b* may be connected to a resistive sensing controller 35*a*. For example, the electrical connector 37 shown in FIG. 1A may connect the probes 27*a* and 27*b* to the resistive sensing controller 35*a*. The resistive sensing controller 35*a* may be a part of the control circuit 35. The first and second leads 26*a* and 26*b* may be connected to a vaporizer driver 35*b* that is a part of the control circuit 35. The vaporizer driver 35*b* may be configured to control the supply of power from the battery section 1 to the heating element 14 through the first and second leads 26*a* and 26*b*.

The resistance R1 of the heating element 14 may be substantially less than the resistance of the wick 28. For example, the resistance of the heating element 14 may be greater than 0Ω and less than 10Ω, but is not limited thereto. The resistance of the heating element may be about 3.5Ω (e.g., 2Ω to 6Ω). The resistance of the wick 28 may be about 10,000Ω to about 50,000,000Ω or more, but may vary depending on design considerations and the resistance R2 of the wick 28 may vary upon the amount of vapor precursor 21 that is saturated onto the wick 28.

The control circuit 35 may utilize known relationships between current, voltage, and resistance, such as Ohm's Law in order to determine the resistance corresponding to various portions (e.g., segments) of the wick 28. After an adult vaper applies negative pressure to the electronic vaping device 60, the control circuit 35 may measure the resistance across one or more of the various portions of the wick 28. The control circuit 35 may be configured to determine the saturation level of the vapor precursor on the wick (or other fluid transport structure such as the heater-wick element 140 in FIGS. 3A and 3B) based on the measured electrical resistance of the portion of the wick (or other fluid transport structure such as the heater-wick element 140 in FIGS. 3A and 3B).

For example, the control circuit 35 may further include a memory 35*c* such as a flash memory device or other non-volatile memory. The memory 35*c* may be used to store values corresponding to resistance measurements of the wick 28. The memory 35*c* may also be used to store reference information that relates a range of resistance measurements of the wick 28 to corresponding estimated saturation levels of vapor precursor on the wick 28. The control circuit may 35 may be configured compare the measured electrical resistance of the wick 28 to the reference information in the memory 35*c* and select an estimate saturation level of vapor precursor based from reference information stored in the memory 35*c*.

Based on how the probes 27*a* and 27*b* are connected to the wick 28 and the first and second leads 26*a* and 26*b* are connected to the heating element 14, the wick 28 may be considered different portions. The control circuit 35 may be configured to measure the electrical resistances of various portions of the wick 28 using different combinations of leads 26*a* and 26*b* and probes 27*a* and 27*b*.

The saturation level of vapor precursor on the wick 28 may change over time after an adult vaper applies negative pressure to the electronic vaping device 60. Accordingly, the control circuit 35 may measure the resistance of one or more portions of the wick 28 immediately after an adult vaper applies negative pressure to the electronic vaping device 60. Alternatively, the control circuit 35 may measure the resistance of one or more portions of the wick 28 within a threshold time (e.g., 10 minutes or less) after an adult vaper applies negative pressure to the electronic vaping device 60.

For example, a first segment of the wick 28 may be considered the part of the wick 28 between the locations where the first probe 27*a* and second probe 27*b* are connected to the wick 28. The first segment of the wick 28 may have resistance R2' as indicated in FIG. 4A. The control circuit 35 may measure the resistance R2' of the wick 28 using the first probe 27*a* and the second probe 27*b*.

A second segment of the wick 28 may be considered the part of the wick 28 between the location of the wick 28 connected to the first probe 27*a* and the location of the wick 28 adjacent to where the first lead 26*a* is connected to the end of heating element 14. The control circuit 35 may measure the resistance of the second segment of the wick 28 using the first probe 27*a* and the first lead 26*a*. A size of the second segment of the wick 28 may be less than a size of the first segment of the wick 28.

A third segment of the wick 28 may be considered the part of the wick 28 between the location of the wick 28 connected to the first probe 27*a* and the location of the wick 28 adjacent to where the second lead 26*b* is connected to the heating element 14. The control circuit 35 may measure the resistance of the third segment of the wick 28 using the first probe 27*a* and the second lead 26*b*. A size of the third segment of the wick 28 may be less than a size of the first segment of the wick 28 and greater than the size of the second segment of the wick 28.

A fourth segment of the wick 28 may be considered the part of the wick 28 between the location of the wick 28 connected to the second probe 27*b* and the location of the wick 28 adjacent to where the first lead 26*a* is connected to the end of heating element 14. The control circuit 35 may be configured to measure the resistance of the fourth segment of the wick 28 using the first lead 26*a* and the second probe 27*b*. A size of the fourth segment of the wick 28 may be less than a size of the first segment of the wick 28, greater than the size of the second segment of the wick 28. The size of the third and fourth segments of the wick 28 may be the same or different.

A fifth segment of the wick 28 may be considered the part of the wick 28 between the location of the wick 28 connected to the second probe 27b and the location of the wick 28 adjacent to where the second lead 26b is connected to the end of heating element 14. The control circuit 35 may be configured to measure the resistance of the fifth segment of the wick 28 using the second lead 26b and the second probe 27b. A size of the fifth segment of the wick 28 may be less than a size of the first segment of the wick 28 and less than a size of the fourth segment of the wick 28. The size of the second and fifth segments of the wick 28 may be the same or different.

The heater-wick structure 140 may have segments that are analogous to the first to fifth segments of the wick 28 described above. For example, just as the first segment of the wick 28 may correspond to the locations of the wick 28 between the locations where the first probe 27a and 27b are connected to the wick 28, a first segment of the heater-wick structure 140 may correspond to the locations of the heater-wick structure 140 between the locations where the first probe 27a and 27b are connected to the heater-wick structure 140. A second segment of the heater-wick structure 140 may correspond to the part of the heater-wick structure 140 between the locations where the first probe 27a and first lead 26a are connected to the heater-wick structure 140. A third segment of the heater-wick structure 140 may correspond to the part of the heater-wick structure 140 between the locations where the first probe 27a and second lead 26b are connected to the heater-wick structure 140. A fourth segment of the heater-wick structure 140 may correspond to the part of the heater-wick structure 140 between the locations where the second probe 27b and first lead 26a are connected to the heater-wick structure 140. A fifth segment of the heater-wick structure 140 may correspond to the part of the heater-wick structure 140 between the locations where the second probe 27b and second lead 26b are connected to the heater-wick structure 140.

Figure 4B:
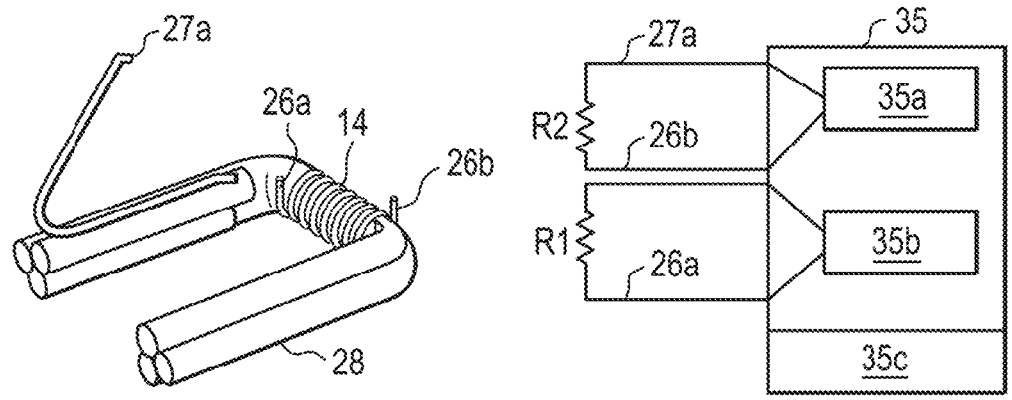
FIG. 4B is a diagram illustrating an electrical connection between a control circuit and a wick in an electronic vaping device according to example embodiments.

FIG. 4B is a diagram illustrating an electrical connection between a control circuit and a wick in an electronic vaping device according to example embodiments.

Referring to FIG. 4B, the wick 28 may include the first probe 27a connected one end of the wick 28, a heating-element (e.g., coil) 14 wrapped around a central portion of the wick 28, and first and second leads 26a and 26b connected to respective ends of the heating element 14. The first probe 27a may be connected to a resistive sensing controller 35a. For example, the electrical connector 37 shown in FIG. 1A may connect first probe 27a to the resistive sensing controller 35a. The resistive sensing controller 35a may be a part of the control circuit 35. The first and second leads 26a and 26b may be connected to a vaporizer driver 35b that is a part of the control circuit 35. The vaporizer driver 35b may be configured to control the supply of power from the battery section 1 to the heating element 14 through the first and second leads 26a and 26b. The second lead 26b may also be connected to the resistive sensing controller 35a.

Referring to FIG. 4B, because the second probe 27b is not connected to the wick 28, the control circuit 35 is not configured to use the second probe 27b for measuring the resistance of the wick 28. However, the control circuit 35 in FIG. 4B is still able to measure the electrical resistance across the second segment of the wick 28 (between the location of the wick 28 connected to the first probe 27a and the location of the wick 28 adjacent to where the first lead 26a is connected to the end of heating element 14) and the electrical resistance across the third segment of the wick 28 (between the location of the wick 28 connected to the first probe 27a and the location of the wick 28 adjacent to where the second lead 26b is connected to the heating element 14) according to the methods described above with reference to FIG. 4A.

Although FIGS. 4A and 4B illustrate non-limiting examples where the vaporizer includes a wick and a heating element, one of ordinary skill in the art would appreciate that the examples in FIGS. 4A and 4B could be applied to other vaporizer structures, such as the heater-wick element 140 in FIGS. 3A and 3B.

Figure 5:
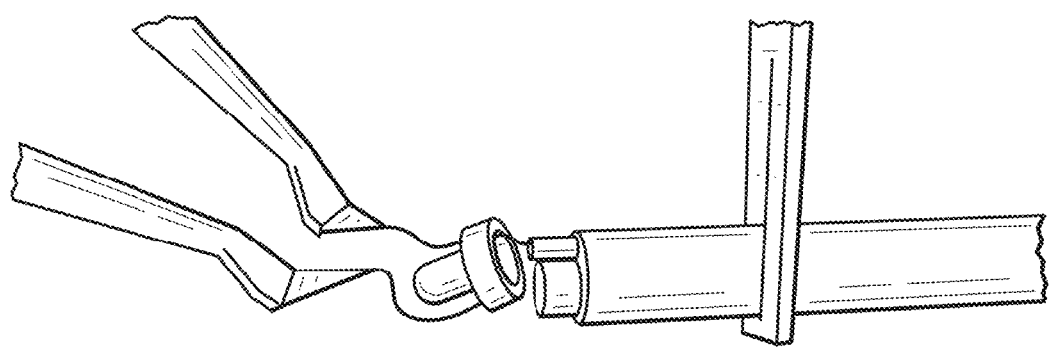
FIG. 5 illustrates an example of a test set up for measuring an electrical resistance across a wick.
Figure 6:
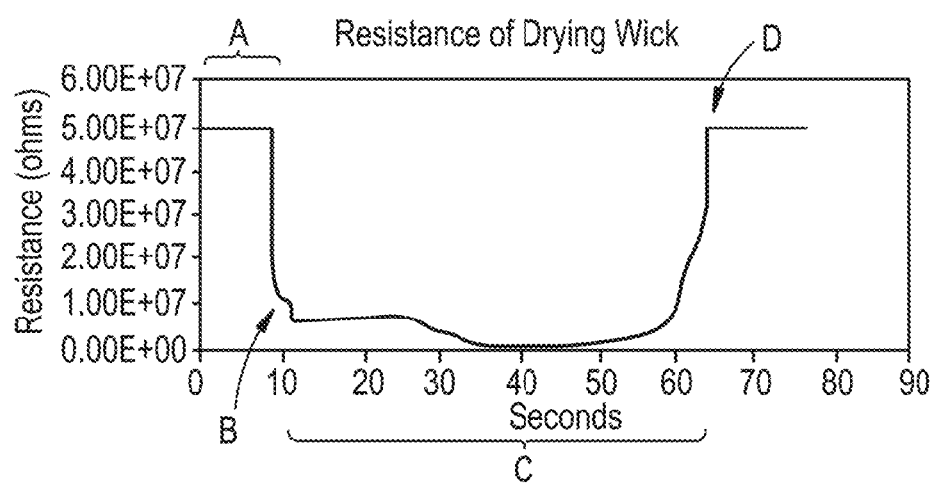
FIG. 6 is graph of the electrical resistance of a drying wick versus time for the example in FIG. 5.

Hereinafter, an experiment measuring the resistance of a drying wick is described with reference to FIGS. 5 and 6. FIG. 5 illustrates an example of a test set up for measuring an electrical resistance across a wick. FIG. 6 is graph of the electrical resistance of a drying wick versus time for the example in FIG. 5.

Referring to FIGS. 5-6, a test device was prepared to measure the electrical resistance of a wick over time at different conditions. The test device includes a tubular body that surrounds a battery. Probes from the left side of FIG. 5 connect an oscilloscope to opposite ends of a wick. The oscilloscope was used to measure the electrical resistance of the wick through the probes. Two wires are connected to the wick at locations that are spaced apart from each other and between the ends of the wick where the probes are connected to the wick. The wires extend from the wick to the tubular body.

During the period A from time of 0 seconds to about 10 seconds, the wick is not saturated with vapor precursor. During period A, the electrical resistance of the wick was relative high at about 50,000,000Ω, based on measurements of the wick using the oscilloscope connected to the wick through the probes. Afterwards, as shown by reference character B in FIG. 6, the electrical resistance is saturated with vapor precursor and the measured electrical resistance of the wick decreases to under 1,000,000Ω, based on measurements of the wick using the oscilloscope connected to the wick through the probes. During the period from C, the vapor precursor on the wick was heated using a heat gun. At around 60 seconds, the resistance of the wick began to increase. As shown by reference character D on FIG. 6, the resistance of the wick eventually returned to the same resistance (or approximately the same resistance) as resistance during period A. In other words, as the wick began to dry out due to vapor precursor evaporation, the electrical resistance of the wick began to increase at around 60 seconds. When the majority of the vapor precursor evaporated and the wick dried out, the measured resistance of the wick reached about 50,000,000Ω (reference character D).

According to example embodiments, a method of operating an electronic device may include measuring an electrical resistance of a fluid-transport structure in a cartomizer of the electronic vapor device using a control circuit in a battery section of the electronic vapor device, and determining a saturation level of the vapor precursor on the fluid-transport structure based on the electrical resistance measurement of the fluid-transport structure. The cartomizer may include a housing, a liquid supply reservoir in the housing, a vaporizer connected to the liquid supply reservoir, and a channel adjacent to the liquid supply reservoir. The vaporizer may include a fluid-transport structure that is configured to transport vapor precursor from the liquid supply reservoir to the channel.

Hereinafter, non-limiting examples of methods of operating an electronic vapor device according to example embodiments are described with reference to FIGS. 7 to 9. The methods discussed in FIGS. 7 to 9 may be implemented using electronic vapor devices according to example embodiments, such as those previously described with reference FIGS. 1A to 1C, 2A to 2C, 3A to 3B, and 4A to 4B.

Figure 7:
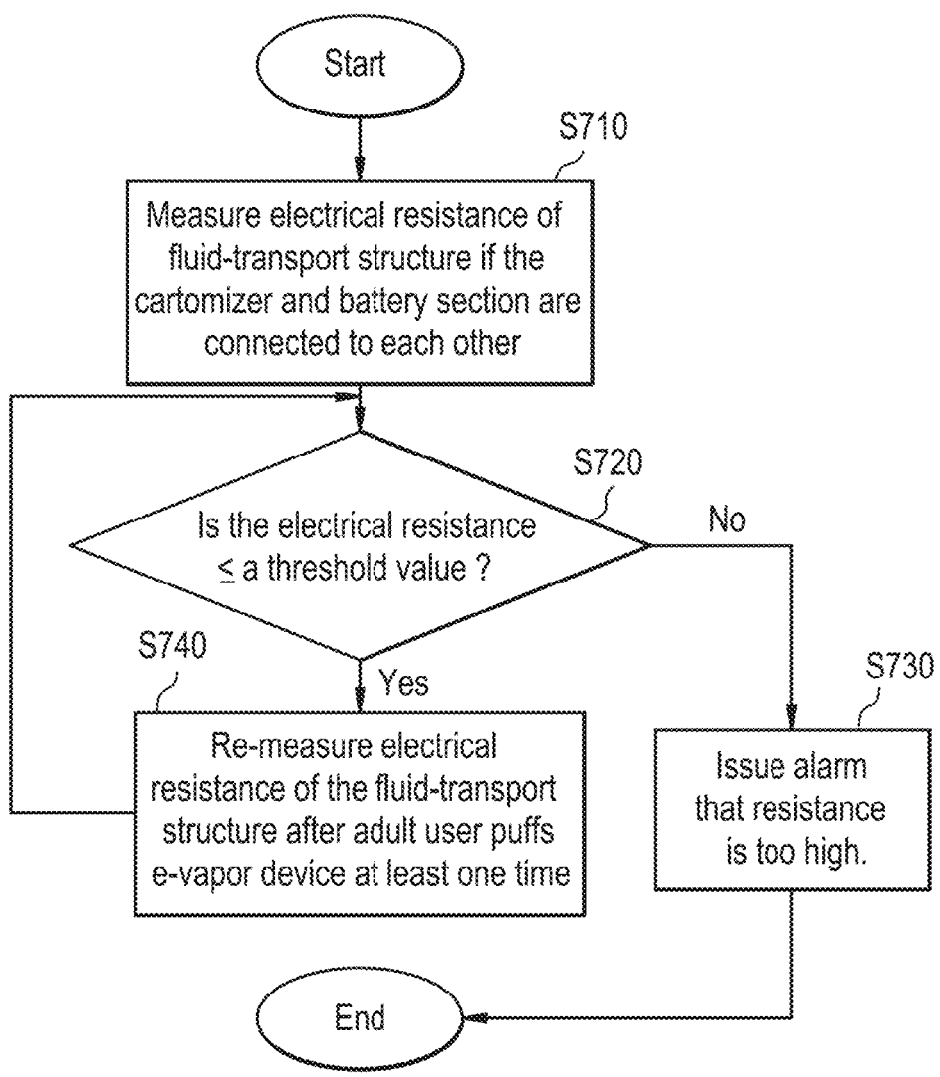
FIG. 7 is a flow chart illustrating a method of operating an electronic vaping device according to example embodiments.

FIG. 7 is a flow chart illustrating a method of operating an electronic vaping device according to example embodiments.

Referring to FIG. 7, in operation S710, the electronic vaping device may determine if the cartomizer 70 and battery section 72 are connected to each other. For example, the control circuit 35 may be connected to a sensor in the battery section 72 that may determine if the cartomizer 70 and battery section 72 are connected to each other. The control circuit 35 may then measure the electrical resistance of a portion of the fluid-transport structure (e.g., wick 28 or heater-wick structure 140) if the cartomizer 70 and battery section 72 are connected to each other.

The portion of the fluid-transport structure measured in operation S710 may correspond to any one of the first to fifth segments of the wick 28 described above with reference to FIGS. 4A and FIG. 4B (if the fluid transport structure is the wick 28) or any one of the analogous first to fifth segments of the heater-wick structure (if the fluid transport structure is the heater-wick stucture).

In operation S720, the control circuit 35 may compare the measured electrical resistance of the portion of the fluid-transport structure to a threshold value. If the measured electrical resistance of the portion of the fluid-transport structure is greater than or equal to the threshold value, then the control circuit 35 may proceed to operation S730 and issue an alarm that the electrical resistance of the portion of the fluid-transport structure is too high.

The control circuit 35 may use different methods to issue an alarm and/or indicate a level of the electrical resistance of the fluid-transport structure. For example, the control circuit 35 may be configured to control the activation light 48 to display a first color if the electrical resistance of the fluid-transport structure is between a first threshold value and a second threshold value. The control circuit 35 may be configured to control the activation light 48 to display a second color if the electrical resistance of the fluid-transport structure is greater than the first threshold value. The first threshold value may be greater than the second threshold value. The first color may be different than the second color.

On the other hand, if the measured electrical resistance of the portion of the fluid transport structure is less than or equal to the threshold value, then the electronic vaping device may proceed to operation S740. In operation S740, electronic vaping device may measure the electrical resistance of the portion of fluid transport structure after an adult vaper applies negative pressure to the mouth end of the electronic vapor device. The portion of the fluid transport structure measured in operation S740 may be the same portion of the fluid transport structure measured in operation S710. In operation S740, the electronic vapor device may use the control circuit 35 to measure the electrical resistance of the portion of fluid transport structure immediately after an adult vaper applies negative pressure to the electronic vaping device. Alternatively, the control circuit 35 may measure the resistance of the portion of the fluid transport structure within a threshold time (e.g., 1 or 5 or 10 minutes or less) after an adult vaper applies negative pressure to the electronic vaping device 60. After operation S740, the electronic vapor device returns to operation S720.

The method in FIG. 7 may include issuing an alarm or re-measuring the electrical resistance after an adult vaper applies negative pressure to the mouth end of the electronic vapor device (e.g., puffs) at least one time, based on the electrical resistance measurement. For example, if the control circuit 35 proceeds from operation S740 back to operation S720, the control circuit 35 may proceed to either operation S730 or operation S740 based on the comparison result at operation S720. If the control circuit 35 proceeds from operation S720 to S740, the control circuit 35 will re-measure the electrical resistance of the portion of the fluid transport structure after an adult vaper applies negative pressure of the mouth end of the electronic vapor device (S740). On the other hand, if the control circuit 35 proceeds from operation S720 to S730, the control circuit may issue an alarm (S730).

In FIG. 7, the saturation level of vapor precursor on the fluid-transport structure may be determined in operation S720 by determining if the electrical resistance of the portion of the fluid-transport structure is less than or equal to a threshold value. Alternatively, in operation S720, the control circuit 35 may determine if the electrical resistance of the portion of the fluid-transport structure is less than a threshold value. The threshold value may be selected based on experimental data and/or empirical study to correspond to a particular saturation level of vapor precursor on the fluid-transport structure. For example, the threshold value in operation S720 may be determined based on a curve similar to FIG. 6 of the present application and selecting an electrical resistance that is between the electrical resistances marked by reference characters B and D in FIG. 6.

One of ordinary skill in the art would appreciate that the method described with reference FIG. 7 could be modified in various ways. For example, for ease of description, the control circuit 35 may measure the electrical resistance of one portion of the fluid transport structure in operations S710 and S740 and then the compare the electrical resistance of the portion to a threshold value. However, example embodiments are not limited thereto. For example, in operations S710 and S740, the control circuit may measure the electrical resistance of at least two different portions of the fluid transport structure and then compare the measured electrical resistance of the at least two portions to corresponding threshold values in operation S720. Then, based on the comparison result, the control circuit 35 may proceed to operation S740 or operation S730.

Figure 8:
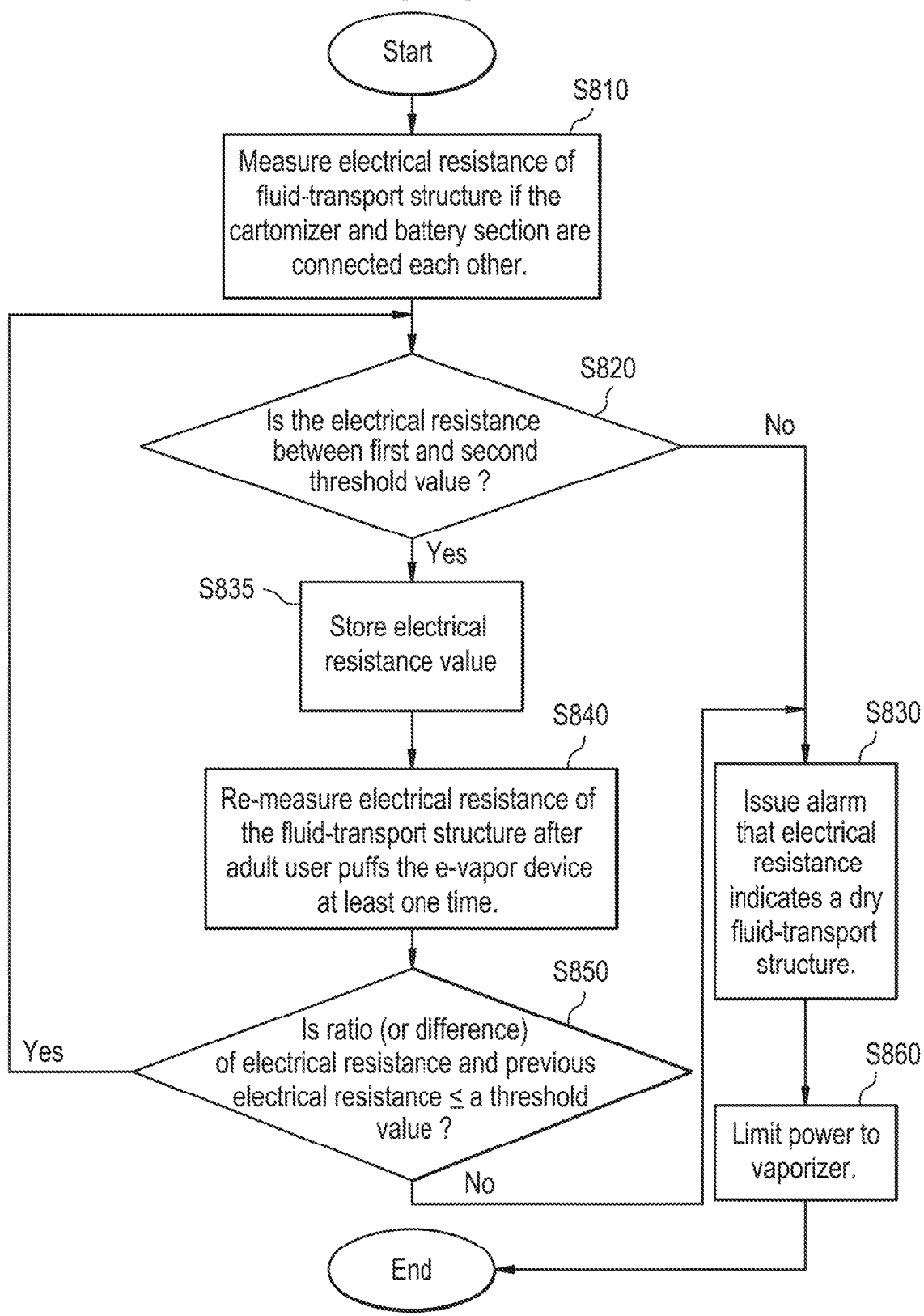
FIG. 8 is a flow chart illustrating a method of operating an electronic vaping device according to example embodiments.

FIG. 8 is a flow chart illustrating a method of operating an electronic vaping device according to example embodiments.

Referring to FIG. 8, in operation S810, the electronic vaping device may determine if the cartomizer 70 and battery section 72 are connected to each other. For example, the control circuit 35 may be connected to a sensor in the battery section 72 that may determine if the cartomizer 70 and battery section 72 are connected to each other. The control circuit 35 may then measure the electrical resistance of a portion of the fluid-transport structure (e.g., wick 28 or heater-wick structure 140) if the cartomizer 70 and battery section 72 are connected to each other.

The portion of the fluid-transport structure measured in operation S810 may correspond to any of the first to fifth segments of the wick 28 described above with reference to FIG. 4A or any of the first to fourth segments of the wick 28 described above with reference to FIG. 4B. Alternatively, if the fluid-transport structure is heater-wick structure 140, the portion of the fluid-transport structure measured in operation S810 may correspond to segments along the heater-wick structure 140 that are analogous to the first to fifth segments of the wick 28 described above with reference to FIGS. 4A and/or 4B.

In operation S820, the control circuit 35 may compare the measured electrical resistance of the portion of the fluid-transport structure to first and second threshold values that are different from each other (e.g., lower and upper control limits). Based on the comparison result in operation S820, the control circuit 35 may proceed to operation S830 or operation S8350. For example, if the measured electrical resistance of the fluid-transport structure is between the first and second threshold values, then the control circuit 35 may proceed to operation S835 and store the measured electrical resistance of the portion of the fluid-transport structure. In operation S835, the measured electrical resistance may be stored in the memory 35c described in FIGS. 4A and 4B. Alternatively, if the measured electrical resistance of the fluid-transport structure is not between the first and second threshold values, then the control circuit 35 may proceed to operation S830, which is described later in more detail.

After operation S835, in operation S840, the control circuit 35 may measure the electrical resistance of the portion of the fluid-transport structure after an adult vaper applies negative pressure to the mouth-end insert 8 of the electronic vaping device at least one time. In other words, the electrical resistance of the portion of the fluid transport structure may be measured after an adult vaper applies negative pressure to the electronic vaping device. For example, the control circuit 35 may measure the electrical resistance of the portion of the fluid-transport structure immediately after an adult vaper applies negative pressure to the mouth-end insert of the electronic vaping device or within a threshold time after an adult vaper applies negative pressure to the mouth-end insert of the electronic vaping device. Alternatively, the control circuit may measure the electrical resistance of the portion of the fluid-transport structure based on a routine, such as measuring the electrical resistance of the portion of the fluid-transport structure immediately after (or within a threshold time) following every N times (N being an integer greater than 1) that the adult vaper applies negative pressure to the mouth-end insert of the electronic vaping device. The portion of the fluid transport structure measured in operations S810 and S840 may be the same portion of the fluid transport structure.

After operation S840, the control circuit 35 may proceed to operation S850. In operation S850, the control circuit may determine a ratio based on the last electrical resistance measurement of the portion of the fluid-transport structure and a reference value. The reference value may be a previous electrical resistance measurement of the portion of the fluid-transport structure, such as the second-to-last most recent electric resistance measurement of the fluid transport structure. In some case, the reference value may correspond to the measurement in operation S810.

In operation S850, the control circuit 35 may compare the ratio based on the last electrical resistance measurement of the portion of the fluid-transport structure and the reference value to a threshold value. For example, control circuit 35 may determine if the ratio is less than or equal to a reference value. The threshold value in operation S850 may be a different threshold value than the first and second threshold values in operation S820. Based on the comparison result in operation S850, the control circuit may proceed to operation S820 or operation S830. For example, if the ratio is less than or equal to the threshold value in operation S850, the control circuit may proceed back to operation S820. If the ratio in operation S850 is greater than the threshold value, then the control circuit may proceed to operation S830. The threshold value may be set based on experimental data and/or empirical study.

In a modification of operation S850, the control circuit 35 may compare a difference based on the last electrical resistance measurement of the portion of the fluid-transport structure and the reference value to threshold value. Based on the comparison result in operation S850, the control circuit may proceed to operation S820 or operation S830. For example, if the difference is less than or equal to the threshold value in operation S850, the control circuit may proceed back to operation S820. If the difference in operation S850 is greater than the threshold value, then the control circuit may proceed to operation S830. The control circuit 35 may use a different threshold value for comparing the difference based on the last electrical resistance measurement of the portion of the fluid-transport structure and the reference value compared to the threshold value used for ratio based on the last electrical resistance measurement of the portion of the fluid-transport structure and the reference value.

In operation S830, the control circuit 35 may issue an alarm based on the comparison result in operation S820 and/or S850. The alarm may be displayed by various methods such as causing the heater activation light 48 to change colors or blink different schemes. The alarm may indicate that the electrical resistance of the portion of the fluid-transport structure corresponds to a dry-fluid transport structure. This signals to an adult vaper that that the cartridge section 70 may need to be changed or the amount of vapor precursor 21 in the liquid supply reservoir 22 may need to be refilled.

After operation S830, the control circuit 35 may proceed to operation S860 and limit and/or terminate the supply of power from the power supply 1 to the vaporizer in the cartridge section 70.

The control circuit 35 may be connected to a light (e.g., the heater activation light 48 or at least one different LED that is not shown on electronic vaping device) and configured to control a color that the light displays based on the electrical resistance measurement of the portion of the fluid-transport structure. For example, the control circuit 35 may be configured to control the light to display a first color if the electrical resistance of the portion of the fluid-transport structure is between the first threshold value and the second threshold value in operation S820. The control circuit 35 may be configured to control the light to display a second color if the electrical resistance of the portion of the fluid-transport structure is not between the first threshold value and the second threshold value in operation S820 and the electrical resistance of the portion of the fluid-transport structure is greater than the larger value among the first and second threshold values in operation S820. The control circuit 35 may be configured to control the light to display a third color if the electrical resistance of the portion of the fluid-transport structure is not between the first threshold value and the second threshold value in operations S820 and the electrical resistance of the portion of the fluid-transport structure is less than the lower value among the first and second threshold values in operation S820. The first to third colors may be different from each other.

Similarly, the control circuit 35 may be configured to control the light to display different colors based on the comparison result in operation S850. The control circuit 35 may include a memory unit such as the memory 35c and the memory 35c is configured to store a plurality of electrical resistance values that correspond to the electrical resistance of the fluid-transport structure measured at different times. The control circuit 35c may be configured to issue an alert based on a comparison result of at least two of the electrical resistance values measured from the fluid-transport structure of a same cartomizer. The at least two of the electrical resistance values may include a first value and a second value, such as the last electrical resistance measurement of the portion of the fluid-transport structure and the reference value discussed above with reference to operation S850. The control circuit is configured to issue the alert if at least one of: a ratio based on the first value and the second value is greater than a threshold ratio; or a difference based on the first value and the second value is greater than a threshold difference.

In FIG. 8, the saturation level of vapor precursor on the fluid-transport structure may be determined in operation S820 by determining if the electrical resistance of the portion of the fluid-transport structure is between the first and second threshold values. The first and second threshold values may be selected based on experimental data and/or empirical study to correspond to particular saturation levels of vapor precursor on the fluid-transport structure. For example, the first and second threshold values in operation S820 may be determined based on a curve similar to FIG. 6 of the present application and selecting first and threshold values that are upper and lower control limits corresponding to a fluid-transport structure that is saturated with vapor precursor (e.g., region C on FIG. 6).

The method in FIG. 8 may include issuing an alarm or re-measuring the electrical resistance after an adult vaper applies negative pressure to mouth end of the electronic vapor device (e.g., puffs) at least one time, based on the electrical resistance measurement. For example, if the control circuit 35 proceeds from operation S850 back to operation S820, the control circuit 35 may proceed to either operations S835 and S840 or operation S830 based on the comparison result at operation S820.

One of ordinary skill in the art would appreciate that FIG. 8 could be modified in various ways. For example, in example embodiments, the control circuit 35 may perform the method in FIG. 8 on more than portion of the fluid transport structure at a time. In other words, in operations S810 and S820, the control circuit 35 may measure the electrical resistance of a first portion of the fluid-transport structure and compare the measured electrical resistance to first and second threshold values corresponding to the first portion of the fluid transport structure. Then, afterwards, the control circuit 35 may perform operations S810 and S820 by measuring the electrical resistance of a second portion of the fluid-transport structure and comparing the measured electrical resistance of the second fluid-transport structures to first and second threshold values corresponding to the second portion of the fluid-transport structure. The control circuit 35 may perform operations S840 and S850 similarly by first performing operations S840 and S850 on the first portion of the fluid-transport structure and then performing operations S840 and S850 on the second portion of the fluid-transport structure.

Figure 9:
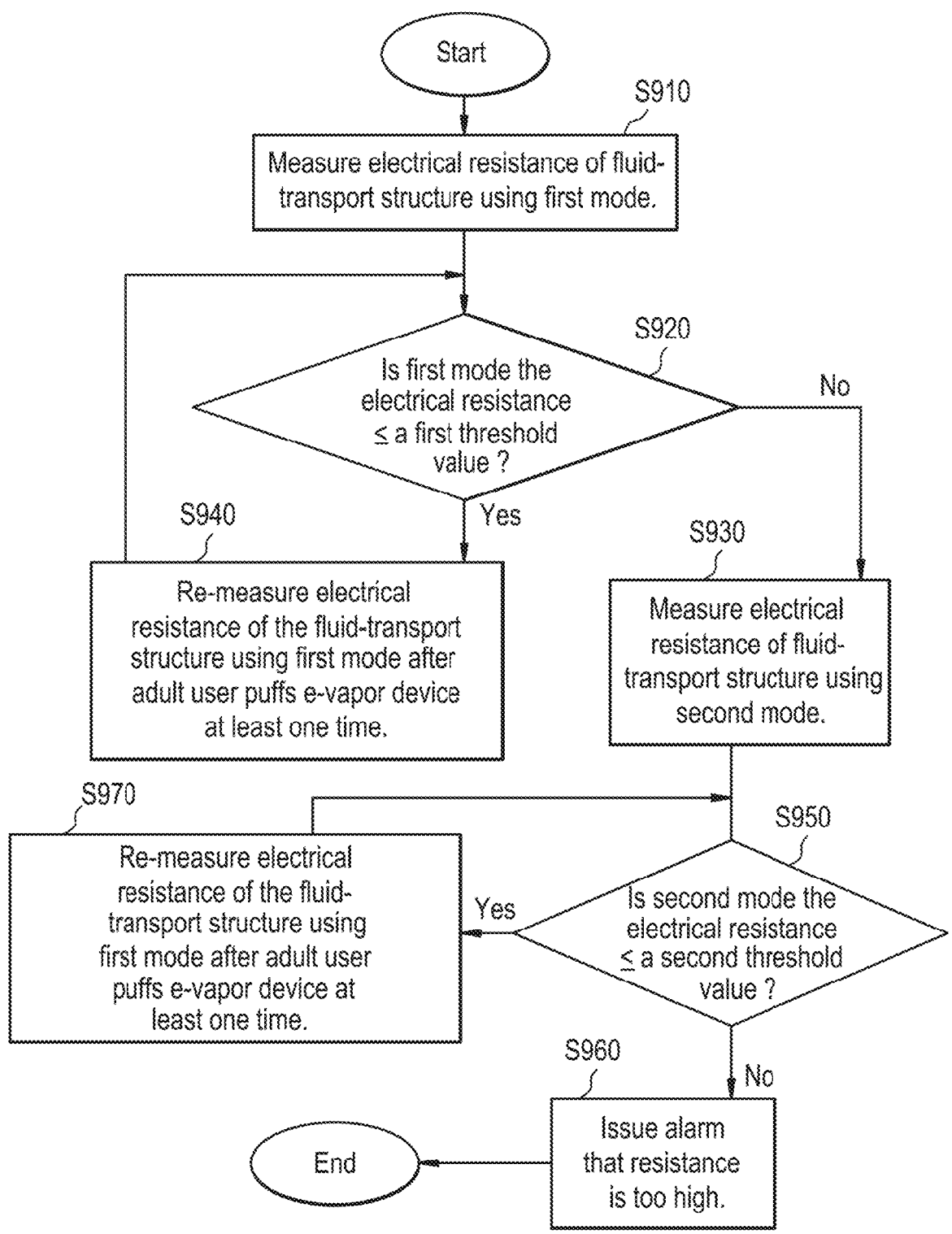
FIG. 9 is a flow chart illustrating a method of operating an electronic vaping device according to example embodiments.

FIG. 9 is a flow chart illustrating a method of operating an electronic vaping device according to example embodiments.

Referring to FIG. 9, in operation S910, the electronic vaping device may determine if the cartomizer 70 and battery section 72 are connected to each other. For example, the control circuit 35 may be connected to a sensor in the battery section 72 that may determine if the cartomizer 70 and battery section 72 are connected to each other. The control circuit 35 may then measure the electrical resistance of a portion of the fluid-transport structure (e.g., wick 28 or heater-wick structure 140) if the cartomizer 70 and battery section 72 are connected to each other.

In operations S910 and S920, the control circuit 35 may measure the electrical resistance of the fluid-transport structure using a first mode (S910) and compare the measured electrical resistance of the fluid-transport structure from the first mode to a first threshold value (S920). For example, the control circuit 35 may determine if the measured electrical resistance from the first mode of the fluid-transport structure (e.g., wick 28 or heater-wick structure 140) is less than or equal to a first threshold value. The first threshold value may be determined through experimental data and/or empirical study.

For operation S910, measuring the electrical resistance of the fluid-transport structure using the first mode may include measuring a first portion of the fluid-transport structure and the first portion of the fluid-transport structure may correspond to any of the first to fifth segments of the wick 28 described above with reference to FIGS. 4A and 4B or the analogous first to fifth segments of the heater-wick structure 140.

Based on the comparison result in operation S920, the control circuit 35 may proceed to operation S930 or operation S940. For example, in operation S920, if the measured electrical resistance of the fluid-transport structure is less than or equal to the first threshold value, then control circuit 35 may proceed to operation S940. In operation S940, the control circuit may re-measure that electrical resistance of the same portion of the fluid transport structure measured in operation S910 after an adult vaper applies negative pressure to the mouth-end insert of the electronic vapor device at least one time (e.g., N times). N may be an integer greater than or equal 1. For example, N may be an integer in a range from 1 to 5 and/or 1 to 10. After operation S940, the control circuit 35 may repeat operation S920.

On the other hand, in operation S920, if the measured electrical resistance of the fluid-transport structure is greater than the first threshold value, the control circuit 35 may proceed to operation S930. In operations S930 and S950, the control circuit 35 may measure the electrical resistance of the fluid-transport structure using a second mode (S930) and compare the measured electrical resistance the fluid-transport structure from the second mode to a second threshold value (S950). For example, the control circuit 35 may determine if the measured electrical resistance from the second mode of the fluid-transport structure (e.g., wick 28 or heater-wick structure 140) is less than or equal to a second threshold value. The second threshold value may be determined through experimental data and/or empirical study. The first and second threshold values in operations S920 and S930 may be the same or different.

For operation S930, measuring the electrical resistance of the fluid-transport structure using the second mode may include measuring a second portion of the fluid-transport structure and the second portion of the fluid-transport structure may correspond to one of the first to fifth segments of the wick 28 described above with reference to FIGS. 4A and 4B or one of the segments along the heater-wick structure 140 that are analogous to the first to fifth segments of the wick 28 described above with reference to FIGS. 4A and/or 4B. The first portion of the fluid-transport structure measured in operations S910 and S940 may be different than the second portion of the fluid-transport structure measured in operation S930.

Based on the comparison result in operation S950, the control circuit 35 may proceed to operation S960 or operation S970. For example, in operation S950, if the measured electrical resistance of portion of the fluid-transport structure is less than or equal to the second threshold value, then control circuit 35 may proceed to operation S970. In operation S970, the control circuit may re-measure that electrical resistance of the same portion of the fluid transport structure measured in operation S930 after an adult vaper applies negative pressure to the mouth-end insert of the electronic vapor device at least one time (e.g., I times). I may be an integer greater than or equal 1. For example, I may be an integer in a range from 1 to 5 and/or 1 to 10. The integer I in operation S950 may be different (e.g., greater than or less than) than the integer N in operation S940. After operation S970, the control circuit 35 may repeat operation S950.

On the other hand, in operation S950, if the measured electrical resistance of the fluid-transport structure is greater than the second threshold value, the control circuit 35 may proceed to operation S960 and issue an alarm that the electrical resistance of the fluid-transport structure is too high. Optionally, the control circuit 35 may also limit and/or prevent power from being supplied to the vaporizer after operation S960.

One of ordinary skill in the art would appreciate that the method in FIG. 9 may be modified in various ways. For example, in operation S920, the control circuit may compare the measured electrical resistance to the first threshold value by determining if the measured electrical resistance is less than the first threshold value instead of less than or equal to the first threshold value. Operation S950 may be modified similarly.

Example embodiments having thus been described, one of ordinary skill in the art would appreciate that example embodiments may be varied in many ways. Such variations are not to be regarded as a departure from the intended spirit and scope of example embodiments, and all such modifications as would be obvious to one skilled in the art are intended to be included within the scope of the following claims.

What is claimed is:

1. A cartomizer comprising:
a housing;
a liquid supply reservoir in the housing;
a vaporizer connected to the liquid supply reservoir, and
a channel adjacent to the liquid supply reservoir,
the liquid supply reservoir being configured to store vapor precursor,
the vaporizer including a fluid-transport structure that extends from the liquid supply reservoir into the channel and is configured to transport the vapor precursor from the liquid supply reservoir to the channel;
a first electrical lead and a second electrical lead connected to a first position and a second position of the vaporizer; and
a probe connected to a third position of the vaporizer,
the first position, the second position, and the third position of the vaporizer being spaced apart from each other, and
the first electrical lead, second electrical lead, and the probe being spaced apart from each other.

2. The cartomizer of claim 1, wherein
the vaporizer includes a heating element that is configured to generate a vapor from the vapor precursor transported to the channel, and
the first position and the second position of the vaporizer are different ends of the heating element.

3. The cartomizer of claim 2, wherein
the fluid-transport structure includes a wick that extends from the channel into the liquid supply reservoir,
the heating element surrounds a portion of the wick in the channel, and
the third position of the vaporizer corresponds to one end of the wick.

4. The cartomizer of claim 2, wherein
the cartomizer includes a mouth-end insert and a seal in the housing at opposite ends of the housing,
the first electrical lead and second electrical lead extend from the first and second positions through the seal to one end of the housing.

5. The cartomizer of claim 4, wherein
the probe extends from the third position of the vaporizer to the one end of the housing.

6. A method of operating an electronic vaping device, the method comprising:
measuring an electrical resistance of a fluid-transport structure in a cartomizer of the electronic vaping device using a control circuit in a battery section of the electronic vaping device,
the cartomizer including a housing, a liquid supply reservoir in the housing, a vaporizer connected to the liquid supply reservoir, and a channel adjacent to the liquid supply reservoir,
the vaporizer including a fluid-transport structure that is configured to transport vapor precursor from the liquid supply reservoir to the channel; and
determining a saturation level of the vapor precursor on the fluid-transport structure based on the electrical resistance measurement of the fluid-transport structure.

7. The method of claim 6, further comprising:
issuing an alarm or re-measuring the electrical resistance after an adult vaper applies negative pressure to the electronic vaping device at least one time, based on the electrical resistance measurement.

8. The method of claim 7, wherein
the determining the saturation level includes determining if the electrical resistance measurement is less than a threshold value,
the issuing the alarm is performed in response to the electrical resistance measurement is greater than the threshold value, and
the re-measuring the electrical resistance after the adult vaper applies negative pressure to the electronic vaping device at least one time is performed in response to the electrical resistance measurement is less than or equal to the threshold value.

9. The method of claim 6, wherein
the determining the saturation level includes determining if the electrical resistance measurement is between a first threshold value and a second threshold value,
the first threshold value is greater than the second threshold value,
the re-measuring the electrical resistance after the adult vaper applies negative pressure to the electronic vaping device at least one time is performed in response to the electrical resistance measurement is between the first and second threshold values.

10. The method of claim 6, wherein
the cartomizer and the battery section are configured to be removably coupled to each other, and
the vaporizer includes a heating element that is configured to generate a vapor from the vapor precursor transported to the channel.

11. A method of making an electronic vaping device, the method comprising:
connecting a cartomizer to a battery section, the cartomizer including a housing, a liquid supply reservoir in the housing, a vaporizer connected to the liquid supply reservoir, and a channel adjacent to the liquid supply reservoir, the liquid supply reservoir configured to store vapor precursor, the vaporizer including a fluid-transport structure that is configured to transport the vapor precursor from the liquid supply reservoir to the channel, the battery section being configured to provide power to the vaporizer, the battery section including a control circuit that is configured to determine a saturation level of the vapor precursor on the fluid-transport structure based on an electrical resistance of the fluid-transport structure.

12. The method of claim 11, wherein
the cartomizer and the battery section are configured to be removably coupled to each other, and
the vaporizer includes a heating element that is configured to generate a vapor from the vapor precursor transported to the channel.

13. The method of claim 12, wherein
the battery section includes a battery,
the fluid-transport structure includes a wick that extends from the channel into the liquid supply reservoir,
the heating element includes a heating coil that is wrapped around a part of the wick, and
the heating coil configured to receive power from the battery and heat the wick.

14. The method of claim 13, wherein
the cartomizer includes a first electrical lead and a second electrical lead that are connected to respective ends of the heating coil,
the cartomizer includes a first probe connected to a first end of the wick,
the first probe and the first electrical lead are separated from each other,
the control circuit is configured to measure the electrical resistance across a portion of the wick using the first probe and one of the first and second electrical leads, and
the control circuit is configured to determine the saturation level of the vapor precursor on the fluid-transport structure based on the measured electrical resistance of the portion of the wick.

15. The method of claim 13, wherein
the cartomizer includes a first probe and a second probe that are electrically connected to a first end and a second of the wick, respectively,
the battery section is configured to connect the first probe and the second probe to the control circuit, and
the control circuit is configured to measure the electrical resistance across the wick using the first probe and the second probe.

16. The method of claim 13, wherein
the cartomizer includes a first probe and a second probe that are electrically connected to a first end and a second end of the wick, respectively,
the cartomizer includes a first electrical lead and a second electrical lead that are connected to respective ends of the heating coil,
the first probe and the first electrical lead are separated from each other,
the second probe and the second electrical lead are separated from each other,
the control circuit is configured to measure the electrical resistance across a first portion of the wick using the first probe and one of the first and second electrical leads,
the control circuit is configured to measure the electrical resistance across a second portion of the wick using the first probe and the second probe,
the control circuit is configured to determine the saturation level of the vapor precursor on the fluid-transport structure based on at least one of the measured electrical resistance across the first portion of the wick and the measured electrical resistance across the second portion of the wick, and
the first portion of the wick and the second portion of the wick are different sizes.

17. The method of claim 14, wherein
the control circuit is configured to measure the electrical resistance across a third portion of the wick using the second probe and at least one of the first electrical lead and the second electrical lead, and
the second portion of the wick and the third portion of the wick are different sizes.

* * * * *